US010300209B2

(12) United States Patent
Stewart

(10) Patent No.: US 10,300,209 B2
(45) Date of Patent: May 28, 2019

(54) FEEDBACK ELEMENT FOR A MEDICAMENT DELIVERY DEVICE

(71) Applicant: Carebay Europe Ltd., Sliema (MT)

(72) Inventor: Justin Stewart, Deerfield Beach, FL (US)

(73) Assignee: SHL Medical AG, Zug (CH)

( * ) Notice: Subject to any disclaimer, the term of this patent is extended or adjusted under 35 U.S.C. 154(b) by 186 days.

(21) Appl. No.: 15/368,348

(22) Filed: Dec. 2, 2016

(65) Prior Publication Data

US 2018/0154083 A1 Jun. 7, 2018

(51) Int. Cl.
*A61M 5/315* (2006.01)
*A61M 5/20* (2006.01)

(52) U.S. Cl.
CPC ........ *A61M 5/3157* (2013.01); *A61M 5/2033* (2013.01); *A61M 5/315* (2013.01); *A61M 2005/2013* (2013.01); *A61M 2205/581* (2013.01); *A61M 2205/582* (2013.01); *A61M 2205/583* (2013.01)

(58) Field of Classification Search
CPC .. A61M 5/3157; A61M 5/2033; A61M 5/315; A61M 2005/2013; A61M 2205/583; A61M 2205/581; A61M 2205/582
See application file for complete search history.

(56) References Cited

U.S. PATENT DOCUMENTS

| 3,807,464 | A | 4/1974 | Pitesky |
| 9,033,934 | B2 | 5/2015 | Karlsson et al. |
| 2008/0077084 | A1 | 3/2008 | Hommann |
| 2012/0310173 | A1* | 12/2012 | Sonderegger ....... A61M 5/2033 604/207 |
| 2013/0096512 | A1* | 4/2013 | Ekman ................. A61M 5/2033 604/197 |
| 2017/0080153 | A1 | 3/2017 | Maxfield |

FOREIGN PATENT DOCUMENTS

| TW | I543788 B | 8/2016 |
| TW | I555547 B | 11/2016 |
| WO | 2011123024 A1 | 10/2011 |
| WO | 2013077800 A1 | 5/2013 |
| WO | 2015121081 A1 | 8/2015 |
| WO | 2016055627 A1 | 4/2016 |
| WO | 2016120587 A1 | 8/2016 |

OTHER PUBLICATIONS

International Search Report issued in International Application No. PCT/EP2017/081082 dated Mar. 27, 2018.
Search Report issued in Taiwanese Patent Application No. 106141861 dated Oct. 19, 2018.

* cited by examiner

*Primary Examiner* — Amber R Stiles
(74) *Attorney, Agent, or Firm* — McDonnell Boehnen Hulbert & Berghoff LLP

(57) ABSTRACT

A feedback element for a medicament delivery device, wherein the feedback element comprises two outer longitudinally extending flexible legs (21*b*) having a proximal and a distal end, and two inner longitudinally extending legs (19) having a proximal and a distal end; wherein the two inner longitudinally extending legs (19) are connected at their proximal ends by a proximal transversal end portion (21*d*) defining a guide extension and wherein each outer longitudinally extending flexible leg (21*b*) is connected to one inner longitudinally extending leg (19) by a distal transversal end portion (21*a*) and wherein each outer longitudinally extending flexible leg (21*b*) extends at its proximal end radially outwards defining a radial foot 21*c*.

15 Claims, 7 Drawing Sheets

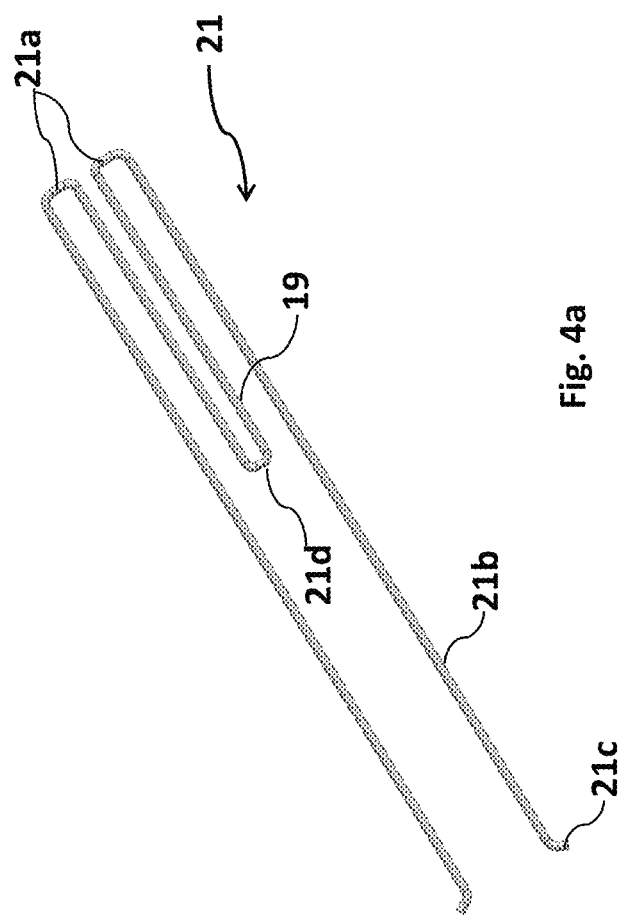

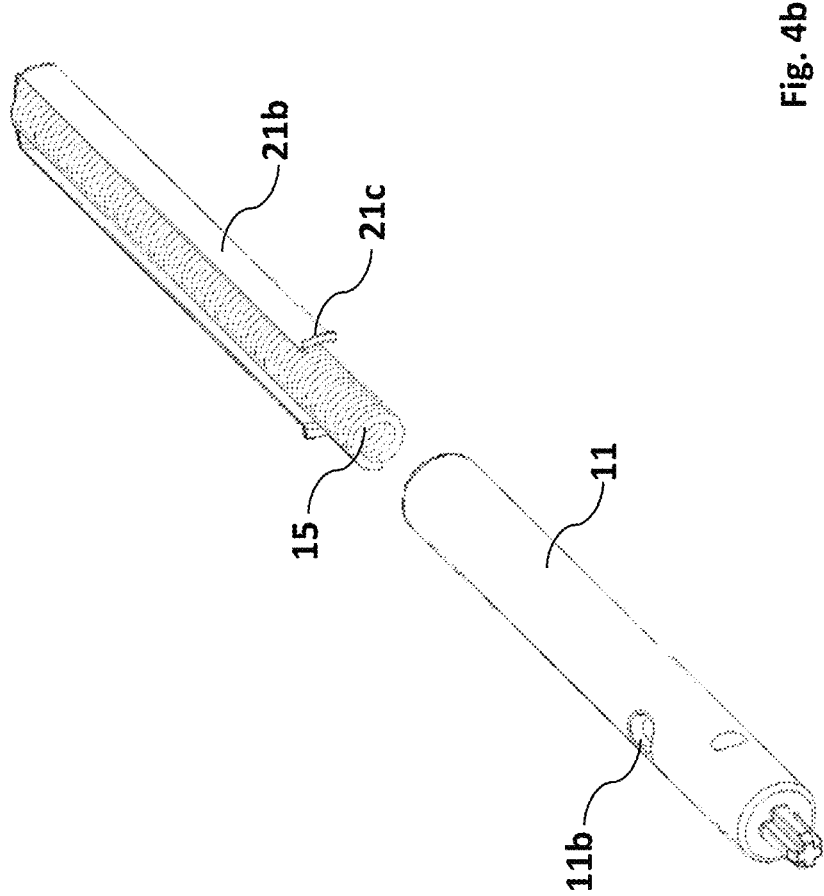

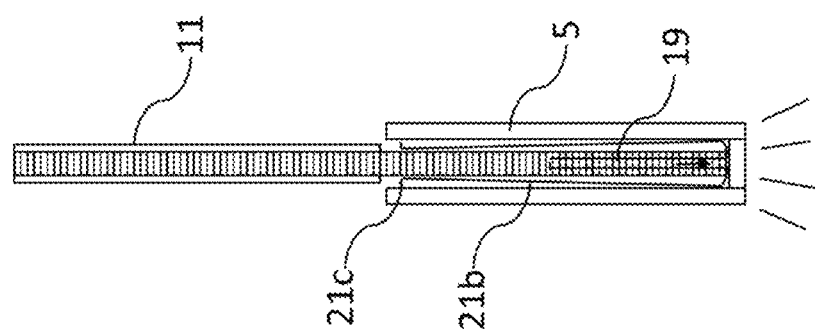
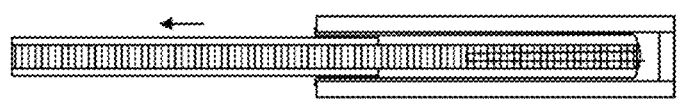
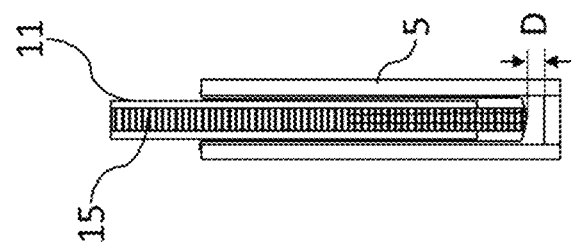
FIG. 6C
FIG. 6B
FIG. 6A

FEEDBACK ELEMENT FOR A MEDICAMENT DELIVERY DEVICE

TECHNICAL FIELD

The present disclosure relates to a feedback element for a medicament delivery device and in particular to an improved element that provides an audible, tactile and/or visual signal or confirmation to a user when a medicament delivery has been made.

BACKGROUND

Medicament delivery devices have been developed for self-administration, i.e. a user performs the medicament delivery by her-, or himself. This requires a medicament delivery device that is safe to use and easy to handle. In order to meet these requirements, the risk of human errors should be minimized, the number of actions needed to be performed in order to receive a dose need to be reduced, and the device should be intuitive and ergonomic to use.

Accordingly, there is a need of enhancing components which are cost effective and fulfil all requirements such that delivery devices minimize the risk of human errors and it is also desirable to have the delivery device that reduce the number of actions needed to be performed in order to receive a dose. There is also a need for a delivery device that provides an enhanced confirmation that a medicament delivery has been completed.

SUMMARY

A general object of the present disclosure is to provide an enhanced feedback element for a medicament delivery device, wherein the feedback element comprises two outer longitudinally extending flexible legs having a proximal and a distal end, and two inner longitudinally extending legs having a proximal and a distal end; wherein the two inner longitudinally extending legs are connected at their proximal ends by a proximal transversal end portion defining a guide extension and wherein each outer longitudinally extending flexible leg is connected to one inner longitudinally extending leg by a distal transversal end portion and wherein each outer longitudinally extending flexible leg extends at its proximal end radially outwards defining a radial foot.

According to an important aspect of the invention is that the feedback element is made of metal and configured as a metal strip or wire. This provides an enhanced feedback confirmation that a medicament delivery has been completed and is also a component which easy and cost effective to manufacture.

It is also an object of the present invention to provide a medicament delivery device that is reliable and easy to use when handling and activating, this is achieved by a medicament delivery device comprising a housing extending along a longitudinal axis and having a distal and proximal end; a plunger rod arranged to be biased towards the proximal end; a first resilient member arranged to be received inside the plunger rod for biasing the plunger rod in the proximal direction; a tubular extension member axially and rotationally fixed relative to the housing; a tubular operation member, arranged to receive a proximal portion of the tubular extension member.

According to another aspect of the invention, the tubular extension member has a radial space defined by an inner perimeter and an inner distal surface and wherein the radial space is arranged to receive the feedback element, the plunger rod and the first resilient member.

According to yet another aspect of the invention, the plunger rod is an elongated hollow body having an external surface, at least one radial opening on the external surface, a proximal transversal wall and a distal end opening, and wherein the plunger rod is arranged to receive the first resilient member through the distal end opening and to houses the guide extension of the feedback element within an internal cavity defined by the first resilient member such that the guide extension prevents buckling of the first resilient member.

According to yet a further aspect of the invention, the first resilient member is arranged to be compressed in a compressed stated wherein the first resilient member is arranged compressed between the distal transverse end portions and the proximal transversal wall inside the plunger rod.

According to another aspect of the invention, the tubular operation member is configured to interact with the tubular extension member to lock the plunger rod in a first position whereby the plunger rod is prevented from axial displacement towards the proximal end and thereby maintain the first resilient member in the compressed state while exerting a force on the plunger rod.

According to yet another aspect of the invention, the distal transversal end portions of the feedback element are distanced by a predetermined distance D from the distal inner surface when the plunger rod in in the first position According to a further aspect of the invention, the legs of the feedback element are configured to bear against the external surface of the plunger rod when the plunger rod is in the first position such that the legs of the feedback element are flexed radially outwards and the radial feet of the feedback element are in engagement with a first engagement means of the tubular extension member.

According to another embodiment, the external surface of the plunger rod may comprise axial grooves configured to receive the legs when the plunger rod is in the first position such that the legs of the feedback element are flexed radially outwards and the radial feet of the feedback element are in engagement with a first engagement means of the tubular extension member.

According to another aspect of the invention, the first engagement means is a proximal end edge or radial recess of the tubular extension member with which the radial feet may engage.

According to yet another aspect of the invention, the tubular operation member is movable relative to the tubular extension member from an initial to a final position such that when the tubular operation member in the initial position, it can press a flexible tongue of the tubular extension member radially inwards to lock the plunger rod in the first position.

According to yet another aspect of the invention, the medicament deliver device further comprises a linearly displaceable medicament delivery member cover configured to interact with the tubular operation member, whereby the tubular operation member is rotatable, by linear displacement of the medicament delivery member cover, between an initial position in which the tubular operation member is arranged to prevent the plunger rod from axial displacement from its first position, and a final position, wherein the tubular operation member and the tubular extension member are arranged to interact such that rotation of the tubular operation member towards the final position releases the plunger rod to allow axial displacement of the plunger rod.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

These as well as other advantages of various aspects of the present patent application will become apparent to those of ordinary skill in the art by reading the following detailed description, with appropriate reference to the accompanying drawings.

BRIEF DESCRIPTION OF THE DRAWINGS

The novel features believed characteristic of the illustrative embodiments are set forth in the appended claims. The illustrative embodiments, however, as well as a preferred mode of use, further structures and descriptions thereof, will best be understood by reference to the following detailed description of an illustrative embodiment of the present disclosure when read in conjunction with the accompanying drawings, wherein:

FIG. 4a is a perspective view of an example of a feedback element;

FIG. 4b is perspective views of an example of a plunger rod, an energy accumulating member and the feedback element;

FIGS. 6A-6C show cross-sectional views of the tubular extension member, the plunger rod and the feedback element in different states of operation.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The medicament delivery device disclosed herein may for example be a disposable single-use medicament delivery device, such as an auto-injector, an inhaler or an eye dispenser. The medicament delivery device may be a regular medicament delivery device for medicament administration, or a trainer device.

The term "proximal end" as used herein refers to that end of a medicament delivery device at which medical injection or expulsion can be provided. This is hence that end of the medicament delivery device that is to be pointed towards the injection or expulsion site. This definition also extends to any internal or external component of the medicament delivery device, i.e. the proximal end of any component is that which is closest to the proximal end of the medicament delivery device. The "distal end" is the opposite end relative to the proximal end. With "proximal direction" is meant a direction from the distal end towards the proximal end, along the central axis of the medicament delivery device. "Distal direction" is meant to be the direction opposite to "proximal direction".

This disclosure concerns an automatic feedback mechanism for a medicament delivery device, and to a medicament delivery device with user feedback capabilities.

Figure 1:
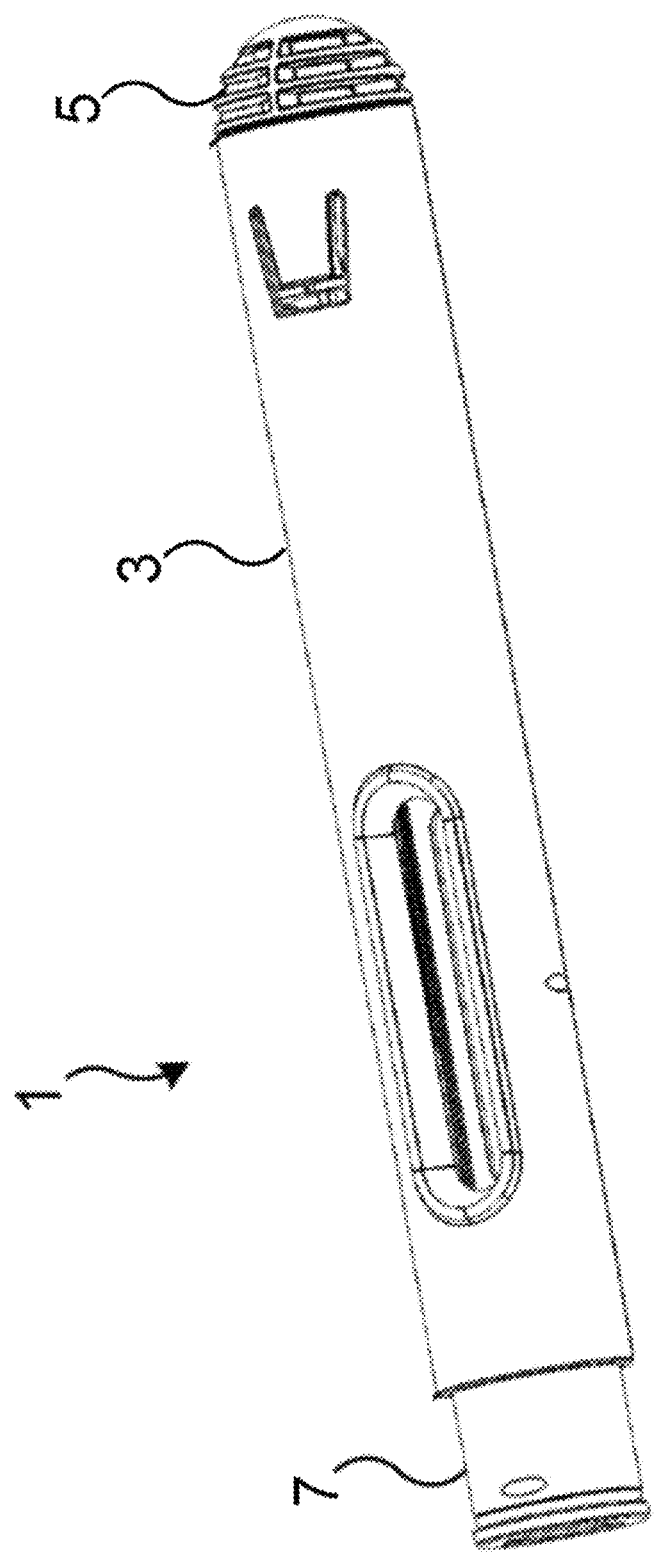
FIG. 1 shows a perspective view of an example of a medicament delivery device.

FIG. 1 shows an example of a medicament delivery device which resides in an initial, non-activated state. The medicament delivery device 1 comprises a housing 3, having a proximal end and a distal end, a tubular extension member 5, for example a rear cap member, mounted at the distal end of the housing 3, and a linearly displaceable medicament delivery member cover 7, e.g. a needle cover, arranged to be received by the housing 3. As illustrated, the exemplified housing 3 comprises a generally tubular shape that comprises a viewing opening or window for allowing a user to determine the position of a plunger within a container that is fixedly contained within the medicament delivery device 1. As such, the viewing opening allows a user to determine whether the medicament delivery device 1 has already been activated to deliver a dose. It is also understood that the exemplified housing 3 or the tubular extension member 5 may further comprise a viewing opening or window (not shown) for providing a user of the medicament delivery device 1 with the ability to view an end of dose indication mechanism after a full dose delivery has been completed.

Figure 2:
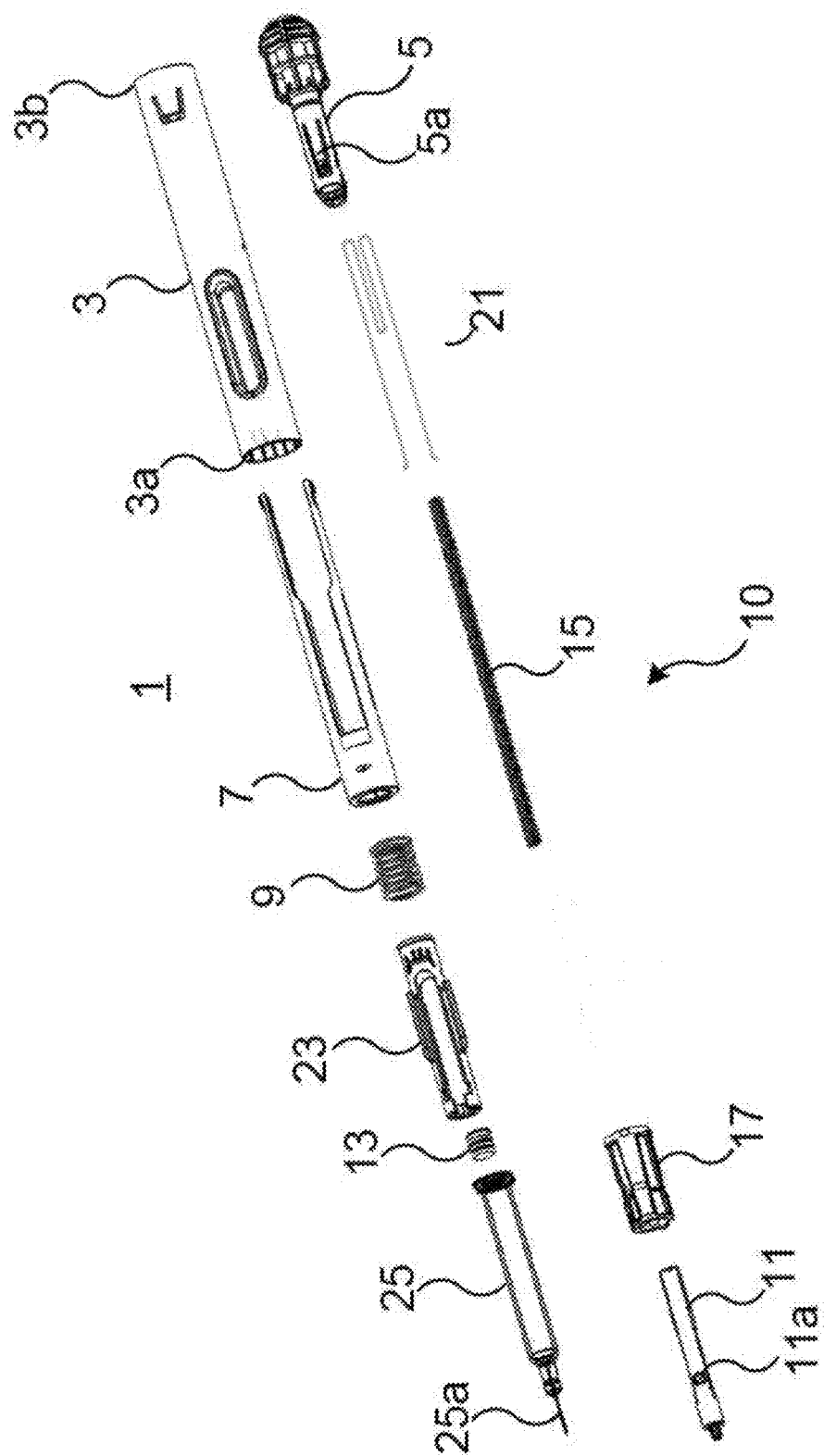
FIG. 2 is an exploded view of the medicament delivery device in FIG. 1.

FIG. 2 depicts an exploded view of the medicament delivery device 1. The medicament delivery device 1 further comprises a plunger rod 11 which is arranged to be biased towards the proximal end; a plunger 13; a first resilient member 15, i.e. an energy accumulation member, arranged to bias the plunger rod 11 in the proximal direction, wherein first resilient member 15 may be a spring for example; a second resilient member or energy accumulation member 9, arranged to bias the medicament delivery member cover 7 in the proximal direction; a feedback element 21; a tubular extension member 5 having a distal and a proximal portion. The tubular extension member 5 has a radial space defined by an inner perimeter and an inner distal surface 5b (FIG. 5) such that this radial space is arranged to receive the feedback element 21, the plunger rod 11 and the first resilient member 15 in the radial space. The tubular extension member 5 is axially and rotationally fixed relative to the housing 3.

The medicament delivery device 1 further comprises a tubular operation member 17, in the following referred to as tubular rotator 17, arranged to receive the proximal portion of tubular extension member 5. The exemplified medicament delivery device 1 further comprises a medicament container holder 23 and a medicament container 25 provided with a needle 25a. The plunger 13 is arranged to run in the medicament container 25 by linear displacement of the plunger rod 11, to thereby expel medicament within the medicament container 25 through the needle 25a.

The plunger rod 11, the tubular extension member 5, the tubular operation member 17, the first resilient member 15 and the feedback element 21 form an automatic feedback mechanism, or simply a feedback mechanism, for the medicament delivery device 1. The feedback mechanism is arranged to notify a user of a finish of expulsion of medicament from the medicament container 25.

Figure 3B:
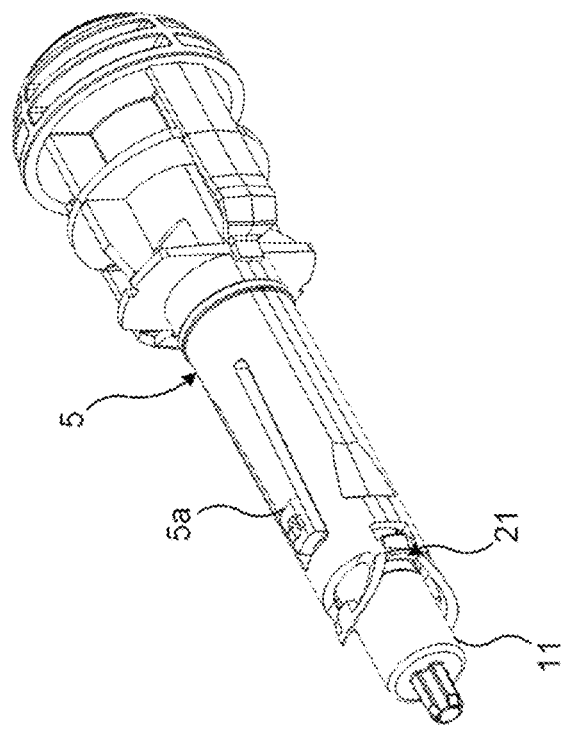
FIG. 3b is a perspective view of one tubular extension member and a plunger rod.

According to the present example, the plunger rod 11 is an elongated hollow body having an external surface, at least one radial opening 11a on the external surface, a proximal transversal wall and a distal end opening. The tubular extension member 5 has flexible tongues 5a configured to releasably lock the plunger rod 11. In more detail, each radial opening 11a is arranged to receive a corresponding flexible tongue 5a which is flexible in the radial direction. The tubular rotator 17 is arranged to receive a proximal portion of the tubular extension member 5, in particular that portion which comprises the flexible tongue 5a. This situation is shown in FIG. 3b. Here, the feedback element 21 received by the tubular extension member 5 can also be seen.

Figure 3A:
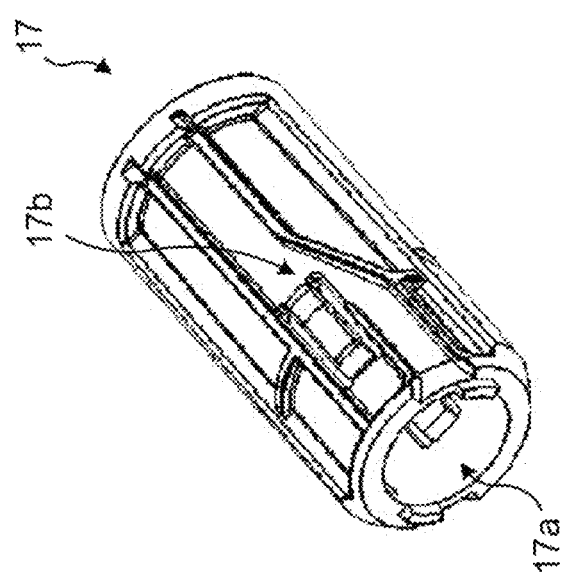
FIG. 3a is a perspective view of one example of a tubular rotator.

FIG. 3a depicts the tubular rotator 17 which comprises a central through-opening 17a extending from the proximal end to the distal end of the tubular rotator 17 and arranged to receive the proximal portion of the tubular extension member 5. The tubular rotator 17 further comprises a guide structure 17b which is arranged to interact with the medicament delivery member cover 7, in particular to convert linear motion of the medicament delivery member cover 7 to rotational motion of the tubular rotator 17. The tubular operation member 17 is configured to interact with the tubular extension member 5 to lock the plunger rod 11 in a first position whereby the plunger rod 11 is prevented from axial displacement towards the proximal end and thereby maintain the first resilient member 15 in a compressed state while exerting a force on the plunger rod 11. In more detail, the tubular rotator 17 is movable i.e. rotatable relative to the tubular extension member 5 from an initial position to a final position. In its initial position the inner structure of the tubular rotator 17 is arranged to push the flexible tongue 5a into engagement with the opening 11a on the plunger rod 11 to lock the plunger rod 11 in the first position. When the medicament delivery member cover 7 is pushed against a delivery site, the medicament delivery member cover 7 moves longitudinally in relation to the housing 3 and towards the distal end whereby the tubular rotator 17 is rotated from the initial position to the final position. The inner structure of the tubular rotator 17 is designed such that when the rotator 17 is in its final position, the inner structure of the tubular rotator 17 will provide less radial force on the flexible tongue 5a, allowing the flexible tongue 5a to flex radially outwards to disengage from the opening 11a on the plunger rod 11. The plunger rod 11, which is biased in the proximal direction, is thereby displaced axially by the first resilient member 15 and medicament administration is thus started as the plunger rod 11 pushes the plunger 13 inside the medicament container 25.

FIG. 4a shows a first example of the feedback element 21. The feedback element 21 comprises two outer longitudinally extending flexible legs 21b having a proximal and a distal end, and two inner longitudinally extending legs 19 having a proximal and a distal end. The two inner longitudinally extending legs 19 are connected at their proximal ends by a proximal transversal end portion 21d defining a guide extension.

Each outer longitudinally extending flexible leg 21b is connected to one inner longitudinally extending leg 19 by a distal transversal end portion 21a. Further, each outer longitudinally extending flexible leg 21b extends at its proximal end radially outwards defining a radial foot 21c.

FIG. 4b shows a first example of the plunger rod 11, the feedback element 21 and the first resilient member 15. The plunger rod 11 is arranged to receive the first resilient member 15 through the distal end opening and to retain the proximal end of the first resilient member 15 in the elongated hollow body to enable biasing by means of the first resilient member 15. Further, the plunger rod 11 may be configured such that the elongated hollow body houses the guide extension 21d of the feedback element 21 within an internal cavity defined by the first resilient member 15. The function of the guide extension 21d is to prevent buckling of the first resilient member 15. The first resilient member 15 is arranged to be compressed between the distal transverse end portions 21a and the proximal transversal wall inside the plunger rod 11. In the first position of the plunger rod 11, the radial feet 21c of the feedback element 21 are in engagement with the tubular extension member 5.

The external surface of the exemplified plunger rod 11 is configured to support the legs 21b of the feedback element 21 such that the legs 21b are prevented to flex radially inwards and thereby enable the radial feet 21c to engage with the tubular extension member 5.

Figure 5:
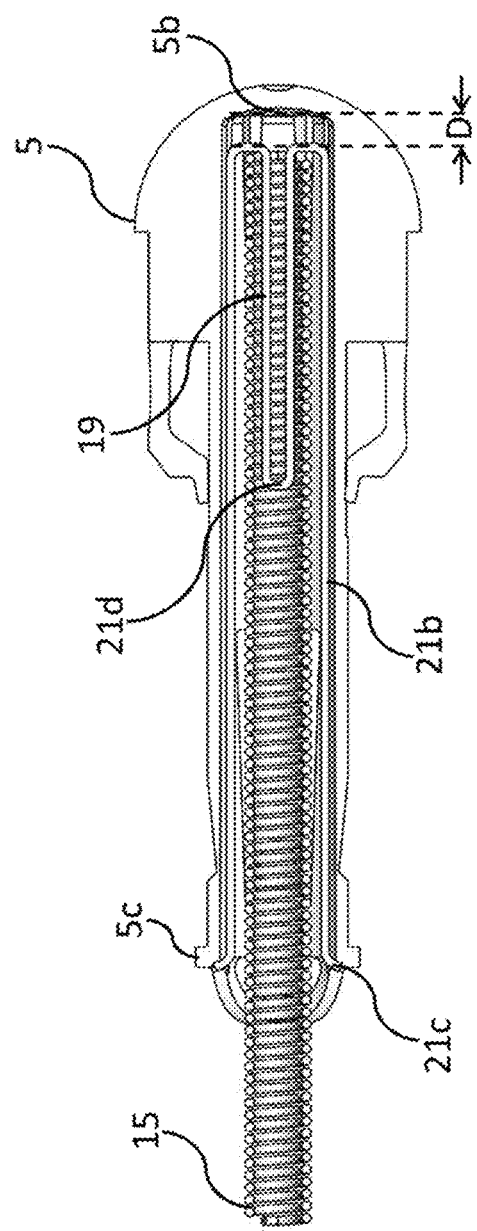
FIG. 5 shows a longitudinal section of a tubular extension member, a first resilient member, and a feedback element in a state.

In FIGS. 5 and 6A the legs 21b of the feedback element 21 bear against the external surface of the plunger rod 11 when the plunger rod 11 is in the first position. The legs 21b of the feedback element 21 are hence flexed radially outwards and the radial feet 21c of the feedback element 21 are in engagement with first engagement means 5c of the tubular extension member 5. The first engagement means 5c may for example be a proximal end edge or radial recess of the tubular extension member 5, with which the radial feet 21c may engage. In other embodiments of the present invention, it is also considered that the exemplified plunger rod 11 has guide structure on its external surface defining axial grooves configured to receive the legs 21b when the plunger rod 11 is in the first position such that the legs 21b of the feedback element 21 are flexed radially outwards and the radial feet 21c of the feedback element 21 are in engagement with a first engagement means 5c of the tubular extension member 5. The guide structure/axial grooves on the external surface of the plunge rod 11 facilitate guiding relative linear movement between the plunger rod 11 and the feedback element 21 whereby the legs 21b may slide in the axial grooves.

The first resilient member 15 is hence in the compressed state, biasing the plunger rod 11 and the feedback element 21 in opposite directions. The tubular extension member 5 has a distal inner surface 5b defining a distal end of the central opening of the tubular extension member 5 in which the plunger rod 11 and the feedback element 21 are arranged. The distal transversal end portions 21a of the feedback element 21 are distanced by a predetermined distance D from the distal inner surface 5b when the plunger rod 11 in in the first position.

In FIG. 6B it is shown when the delivery procedure is initiated and the plunger rod 11 has started to move from the first position to a second position for pushing the plunger 13 inside the medicament container 25. To initiate the delivery procedure, the medicament delivery member cover 7 is pressed against a delivery site whereby linear motion of the medicament delivery member cover 7 converts to rotational motion of the tubular rotator 17 due to the interaction with the tubular rotator 17. The tubular rotator 17 is rotated from the initial position to the final position whereby the inner structure of the tubular rotator 17 will provide less radial force on the flexible tongue 5a, allowing the flexible tongue 5a to flex radially outwards to disengage from the opening 11a on the plunger rod 11. The plunger rod 11, which is biased in the proximal direction, is thereby displaced axially and medicament administration is thus started as the plunger rod 15 pushes the plunger 13 inside the medicament container 25.

In FIG. 6c it is shown when plunger rod is in the second position. The distal end of the plunger rod 11 has passed the radial feet 21c of the feedback element 21 such that these radial feet 21c are released from engagement with the first engagement means 5c of the tubular extension member 5, whereby the legs 21b of the feedback element 21 are able to flex radially inwards towards its radially unbiased position. This radial inwards flexing of the legs 21b of the feedback element 21 is sufficient to disengage the radial feet 21c from the first engagement means 5c of the tubular extension member 5. Then, the feedback element 21 can be rapidly displaced in the distal direction by the force of the first resilient member 15 until the distal transversal end portions 21a of the feedback element 21 reaches/hits the distal inner surface 5b of the tubular extension member 5. This collision results in an audible "click" and in vibration of the medicament delivery device 1. The user hence becomes aware of that medicament injection or expulsion has finished. The user may then, for example, count 10-15 seconds before removing the medicament delivery device 1 from the injection site.

In the present embodiment, the feedback element 21 is made of metal for giving an enhanced audible "click" and vibration. However it is also considerable that it can be made of plastic or any other material. In one preferred embodiment, the feedback element 21 is a metal strip or wire. The feedback element provides a more compact and simple design which also allows a simpler and easy assembly process.

In one preferred arrangement, the distal ends of the legs 21b may comprise a visual indicator which may be a coloured portion and/or visual indicating symbols. This visual indicator is viewable by a user of the medicament delivery device 1 through a window or opening in the tubular extension member 5 after a completed dose delivery The description has mainly been described above with reference to a few examples of different advantageous embodiments for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

The invention claimed is:

1. A feedback element for a medicament delivery device, wherein the feedback element comprises:
   two outer longitudinally extending flexible legs having a proximal and a distal end, and
   two inner longitudinally extending legs having a proximal and a distal end,
   wherein the two inner longitudinally extending legs are connected at their proximal ends by a proximal transversal end portion defining a guide extension,
   wherein each outer longitudinally extending flexible leg is connected to one inner longitudinally extending leg by a distal transversal end portion,
   wherein each outer longitudinally extending flexible leg extends at its proximal end radially outwards in a same plane as formed by the two inner longitudinally extending legs, and
   wherein each proximal end of each outer longitudinally extending flexible leg defines a radial foot.

2. The feedback element for the medicament delivery device according to claim 1, wherein the feedback element is made of metal.

3. The feedback element for the medicament delivery device according to claim 1, wherein the feedback element is a metal strip or wire.

4. A medicament delivery device comprising:
   a feedback element, wherein the feedback element comprises:
      two outer longitudinally extending flexible legs having a proximal and a distal end, and
      two inner longitudinally extending legs having a proximal and a distal end,
      wherein the two inner longitudinally extending legs are connected at their proximal ends by a proximal transversal end portion defining a guide extension,
      wherein each outer longitudinally extending flexible leg is connected to one inner longitudinally extending leg by a distal transversal end portion,
      wherein each outer longitudinally extending flexible leg extends at its proximal end radially outwards in a same plane as formed by the two inner longitudinally extending legs, and
      wherein each proximal end of each outer longitudinally extending flexible leg defines a radial foot.

5. The medicament delivery device according to claim 4, further comprising:
   a housing extending along a longitudinal axis and having a distal and proximal end;
   a plunger rod arranged to be biased towards the proximal end;
   a first resilient member arranged to be received inside the plunger rod for biasing the plunger rod in the proximal direction;
   a tubular extension member axially and rotationally fixed relative to the housing; and
   a tubular operation member, arranged to receive a proximal portion of the tubular extension member.

6. The medicament delivery device according to claim 5, wherein the tubular extension member has a radial space defined by an inner perimeter and an inner distal surface, and wherein the radial space is arranged to receive the feedback element, the plunger rod, and the first resilient member.

7. The medicament delivery device according to claim 6, wherein the plunger rod is an elongated hollow body having an external surface, at least one radial opening on the external surface, a proximal transversal wall, and a distal end opening, and
   wherein the plunger rod is arranged to receive the first resilient member through the distal end opening and to houses the guide extension of the feedback element within an internal cavity defined by the first resilient member such that the guide extension prevents buckling of the first resilient member.

8. The medicament delivery device according to claim 7, wherein the first resilient member is arranged to be compressed in a compressed state, wherein the first resilient member is arranged to be compressed between the distal transverse end portions and the proximal transversal wall inside the plunger rod.

9. The medicament delivery device according to claim 8, wherein the tubular operation member is configured to interact with the tubular extension member to lock the plunger rod in a first position whereby the plunger rod is prevented from axial displacement towards the proximal end and thereby maintain the first resilient member in the compressed state while exerting a force on the plunger rod.

10. The medicament delivery device according to claim 9, wherein the distal transversal end portions of the feedback element are distanced by a predetermined distance D from the distal inner surface when the plunger rod in in the first position.

11. The medicament delivery device according to claim 10, wherein the two outer longitudinally extending flexible legs of the feedback element are configured to bear against the external surface of the plunger rod when the plunger rod is in the first position such that the two outer longitudinally extending flexible legs of the feedback element are flexed radially outwards and the radial feet of the feedback element are in engagement with a first engagement means of the tubular extension member.

12. The medicament delivery device according to claim 10, wherein the external surface of the plunger rod comprises axial grooves configured to receive the two outer longitudinally extending flexible legs when the plunger rod is in the first position such that the two outer longitudinally extending flexible legs of the feedback element are flexed radially outwards and the radial feet of the feedback element are in engagement with a first engagement means of the tubular extension member.

13. The medicament delivery device according to claim 11, wherein the first engagement means is a proximal end edge or radial recess of the tubular extension member with which the radial feet may engage.

14. The medicament delivery device according to claim 6, wherein the tubular operation member is movable relative to the tubular extension member from an initial to a final position such that when the tubular operation member is in the initial position, the tubular operation member presses a flexible tongue of the tubular extension member radially inwards to lock the plunger rod in the initial position.

15. The medicament deliver device of claim 14, further comprising a linearly displaceable medicament delivery member cover configured to interact with the tubular operation member and move the tubular operation member from the initial position to the final position.

* * * * *